(12) United States Patent
Meurer et al.

(10) Patent No.: US 11,678,864 B2
(45) Date of Patent: Jun. 20, 2023

(54) MODULAR ULTRASOUND PROBE MANAGEMENT SYSTEM

(71) Applicant: GE Precision Healthcare LLC, Wauwatosa, WI (US)

(72) Inventors: Robert A. Meurer, Waukesha, WI (US); Emily Elizabeth Siira, Waukesha, WI (US); Ross Christopher Stalter, Hartland, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 254 days.

(21) Appl. No.: 17/166,125

(22) Filed: Feb. 3, 2021

(65) Prior Publication Data
US 2022/0240896 A1 Aug. 4, 2022

(51) Int. Cl.
*A61B 8/00* (2006.01)
(52) U.S. Cl.
CPC .............. *A61B 8/4405* (2013.01); *A61B 8/42* (2013.01); *A61B 8/4411* (2013.01); *A61B 8/4427* (2013.01)
(58) Field of Classification Search
CPC ........................... A61B 8/4405; A61B 8/4411
See application file for complete search history.

(56) References Cited

U.S. PATENT DOCUMENTS

| 5,505,203 A | * | 4/1996 | Deitrich | G01S 15/899 600/459 |
| 5,615,678 A | * | 4/1997 | Kirkham | A61B 8/44 600/459 |
| 2003/0236463 A1 | * | 12/2003 | Mesaros | A61B 8/00 600/459 |
| 2015/0025389 A1 | * | 1/2015 | Murphy | A61B 8/4455 600/459 |
| 2017/0150944 A1 | * | 6/2017 | Kim | A61B 8/4444 |
| 2019/0380681 A1 | * | 12/2019 | Meurer | A61B 8/4427 |

FOREIGN PATENT DOCUMENTS

WO  WO-2015059597 A1 * 4/2015 ........... A61B 8/4405

* cited by examiner

*Primary Examiner* — Colin T. Sakamoto
(74) *Attorney, Agent, or Firm* — Boyle Fredrickson, S.C.

(57) ABSTRACT

A portable ultrasound imaging assembly includes a probe management system to facilitate the positioning of accessories, such as containers and/or probes of various types and associated cords utilized with a portable ultrasound imaging system forming a part of the ultrasound imaging assembly. The probe management system includes dedicated attachment locations and/or handles that enable a user to readily grasp, move and carry the imaging assembly or components thereof into the desired position. The attachment locations and/or handles are formed with uniform cross-sectional shapes and include mounting locations thereon where various probe/accessory holders can be removably secured. The holders are formed with clips that conform to the cross-sectional shape of the attachment locations/handles, such that the holders can be mounted in a modular manner to either handle in the desired mounting location.

16 Claims, 13 Drawing Sheets

MODULAR ULTRASOUND PROBE MANAGEMENT SYSTEM

BACKGROUND OF THE INVENTION

Embodiments of the subject matter disclosed herein relate to diagnostic medical imaging, and more particularly, to ultrasound imaging devices and workstations.

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device. In one example, the display device may be a touch-sensitive display, also referred to as a touchscreen. A user may interact with the touchscreen to analyze the displayed image. For example, a user may use their fingers on the touchscreen to position a region of interest (ROI), place measurement calipers, or the like.

In ultrasound imaging systems that are used as point of care devices, e.g., devices that are mobile and/or that are employed at the patient bedside, or quickly wheeled or carried into tight spaces, in critical and compromising situations, such as emergency rooms or surgical operations, the systems are formed as part of an ultrasound imaging assembly including a support stand or cart that can readily be moved to position the ultrasound imaging system where desired. The ultrasound imaging system can be disposed on the support stand in a manner that enables the ultrasound imaging system to be readily employed to obtain images of the patient at the particular use location. With certain ultrasound imaging systems, components of the imaging system, such as the display device, can be removed from the support stand to further enhance the mobility and utility of the point of care ultrasound imaging system.

In these types of ultrasound imaging assemblies and systems, the probes, as well as other components of the imaging system, are connected using cables extending from the probe and terminating in a plug which is inserted into the corresponding component, such as the display device. When not in use the probe is placed within a suitable storage location disposed on the support stand/cart.

However, the cables connecting the probes and other components to the ultrasound imaging system must have a sufficient length in order to extend from the imaging system disposed on the cart to the patient during use of the ultrasound imaging system. As a result, when not in use the cords loop downwardly from the locations where the probes are stored. Due to the length of the cords and the mobile nature of the ultrasound imaging assembly and cart, the management of the cables connecting the various components of the ultrasound imaging system to one another creates issues with design for prior art support stands/carts of point of use ultrasound imaging systems. More specifically, the length of the cords often allows the cords to contact the ground around the cart when the associated probe is not in use. As such, when the cart is moved the cart can be rolled over the cords, the user can trip over the cords, or other entanglement issues with the cords can occur, causing the probes to become dislodged from the storage locations on the cart and damaged as a result of falling to the ground. Additionally, the cords can easily become tangled with one another, further complicating use of the point of use ultrasound imaging system.

As a result, it is desirable to develop a system and structure capable of managing cords from probes used in a portable ultrasound imaging system to minimize and eliminate these issues with prior art systems.

BRIEF DESCRIPTION OF THE DISCLOSURE

The present disclosure, a portable ultrasound imaging assembly includes a probe management system to facilitate the positioning of accessories, such as containers and/or probes of various types and associated cords utilized with a portable ultrasound imaging system forming a part of the ultrasound imaging assembly. The probe management system includes dedicated attachment locations and/or handles located on the support stand or cart for the imaging assembly that enable a user to readily grasp and move the imaging assembly into the desired position. The attachment locations and/or handles are formed with uniform cross-sectional shapes and include mounting locations thereon where various probe/accessory holders can be removably secured. The holders are formed with clips that conform to the cross-sectional shape of the attachment locations/handles, such that the holders can be mounted in a modular manner to either handle in the desired mounting location. As such, the attachment locations/handles and holders enable the probes and other accessories used with the ultrasound imaging assembly and ultrasound imaging system to be reconfigured in customizable positions to accommodate for the particular environment in which the ultrasound imaging assembly is being utilized.

The probe management system also includes umber of cord management features disposed within the probe management system. In certain embodiment of the disclosure, the cord management features are disposed on the handles and provide locations for the positioning of probe cords in locations that minimizes the cords from becoming entangled with one another and from extending downwardly from the handle to the surface on which the support stand or cart is placed, preventing contact of the cords with the surface and/or the wheels supporting the stand or cart on the surface.

According to another aspect of the disclosure, a portable ultrasound imaging system including an imaging device, a number of attachment locations connected to the imaging device and at least one accessory holder removably connected to the number of attachment locations.

According to another aspect of the disclosure, the portable ultrasound imaging system, includes a support stand, a central handle secured to the support stand, an imaging device removably attached to the support stand above the central handle, a device carrying handle secured to the imaging device and at least one accessory holder removably connected to at least one of the central handle and the device carrying handle.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The foregoing summary, as well as the following detailed description of certain embodiments of the present invention, will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
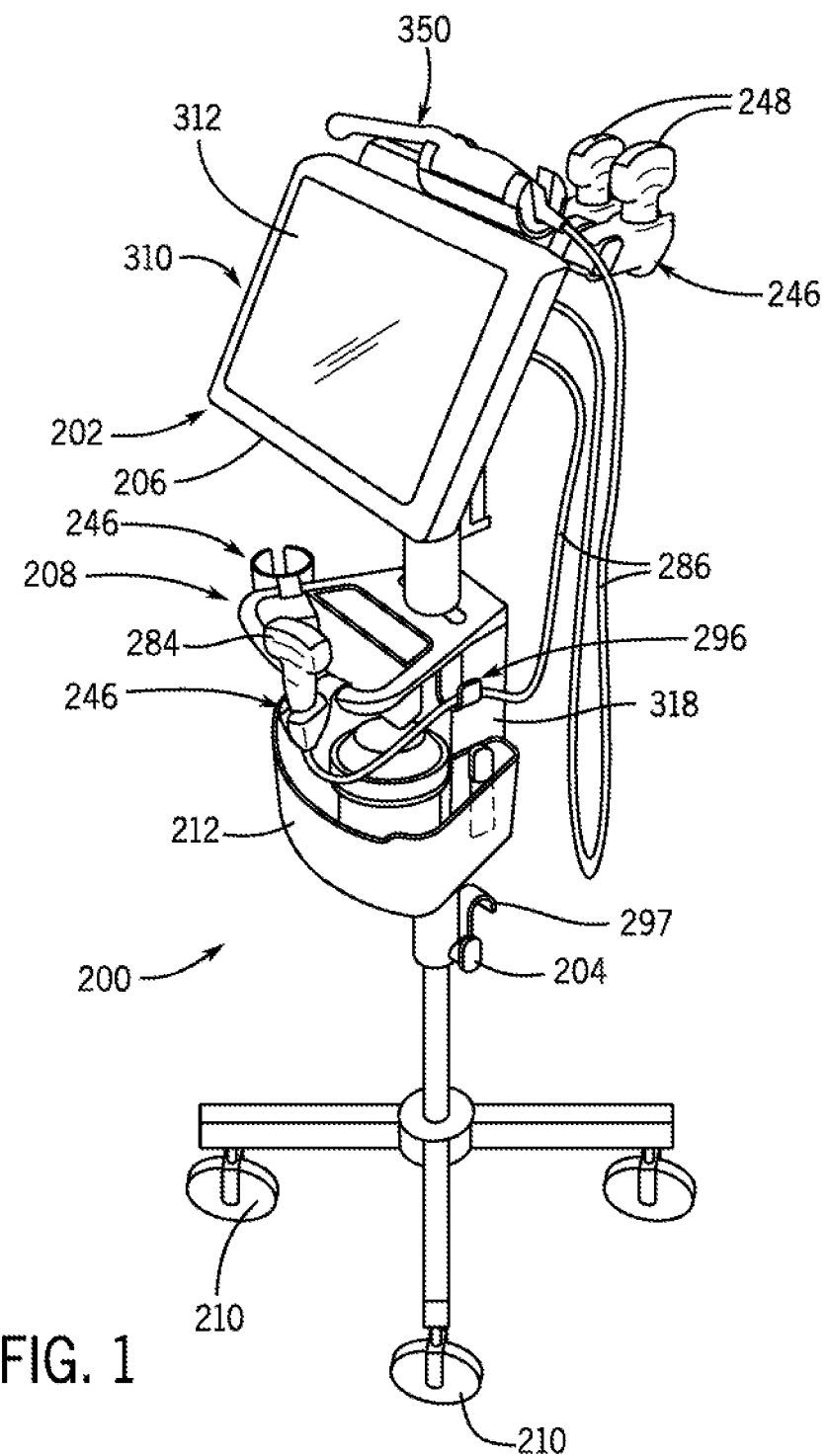
FIG. 1 shows an example portable ultrasound imaging assembly, according to an embodiment of the invention.

As shown in FIG. 1, an ultrasound imaging assembly 200 is shown. The ultrasound imaging assembly 200 includes portable ultrasound system 202. In one example, the portable ultrasound system 202 is similar to that disclosed in US Patent Application Publication No. US2019/0380681 entitled *Method And Systems For A Portable Ultrasound Imaging System*, the entirety of which is expressly incorporated herein by reference for all purposes. The portable ultrasound system 202 is a unitary system that is capable of being separated (e.g., decoupled) from a remainder of the ultrasound imaging assembly 200 and may be moved (e.g., portably) from room to room relative to the remainder of the ultrasound imaging assembly 200 which may stay in place and/or not be moved with the portable ultrasound system 202.

Figure 2:
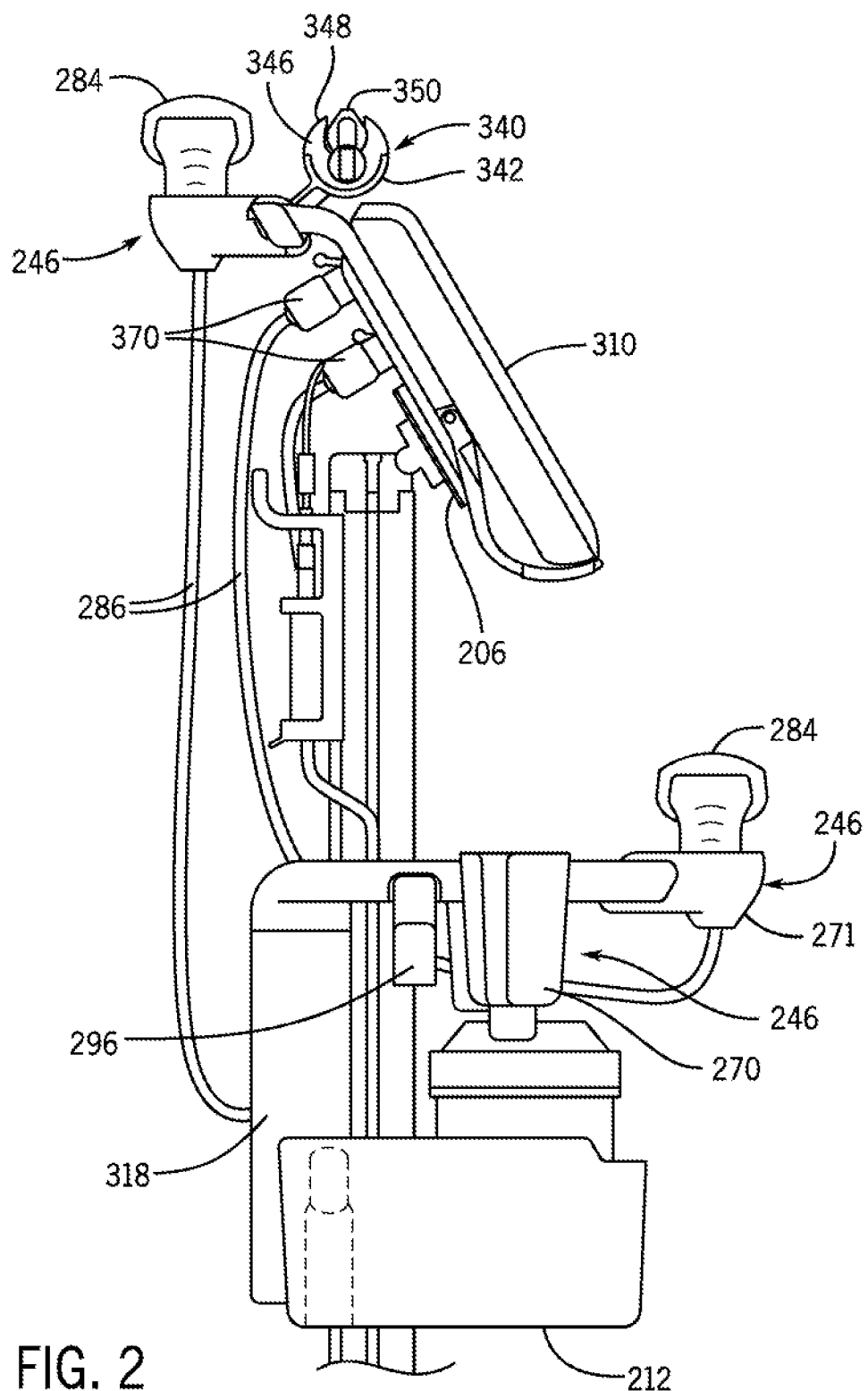
FIG. 2 is a partially broken away, side elevation view of the portable ultrasound imaging, assembly shown in FIG. 1 in accordance with an embodiment.
Figure 3:
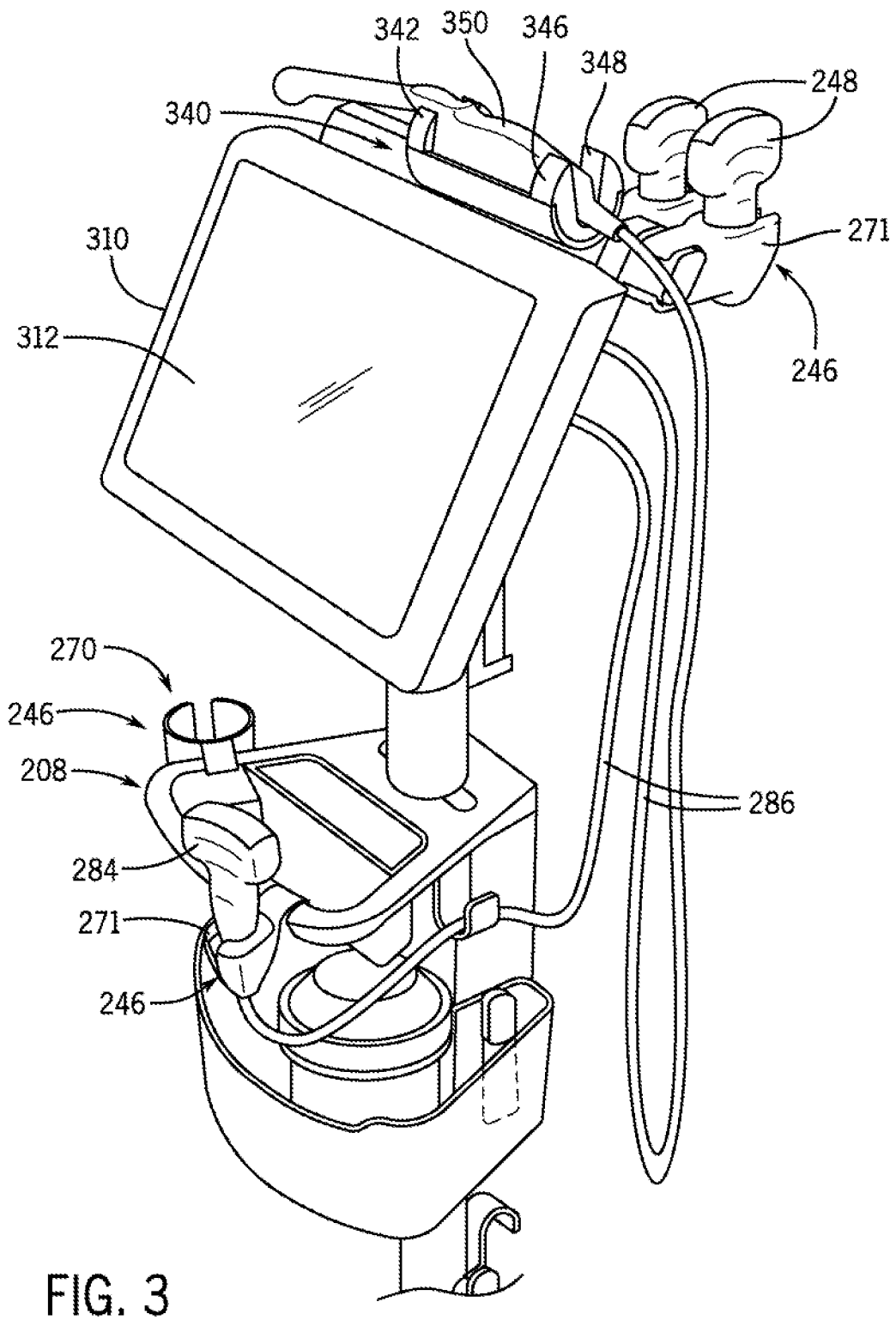
FIG. 3 is a partially broken away, front isometric view of the portable ultrasound imaging assembly of FIG. 2 in accordance with an embodiment.

As shown in the views shown by FIGS. 1-3, ultrasound imaging assembly 200 includes support stand 204, and each of a central handle 20S, a storage container 212, and cradle 206 coupled to the support stand 204. Specifically, the central handle 208 and storage container 212 are shown coupled to the support stand 204 between a first end 250 and a second end 252, with the cradle 206 positioned at the first end 250 and with a plurality of casters 210 of the support stand 204 positioned at the second end 252. Casters 210 are configured to support the support stand 204 against ground surface 260 and to enable the support stand 204 to more easily move across the ground surface 260 (e.g., roll along the ground surface 260). The z-axis of reference axes 279 is an axis positioned vertical relative to the ground surface 260 (e.g., extending in a vertical, normal direction relative to ground surface 260). In some examples, one or more of the casters 210 may be configured with a locking mechanism (e.g., a brake) configured to selectively lock the casters 210 and maintain a position of the support stand 204 relative to the ground surface 260 (e.g., reduce a likelihood of the casters 210 from rolling or otherwise moving relative to the ground surface 260).

FIGS. 1-7 additionally show the central handle 208 coupled to the support stand 204 of the ultrasound imaging assembly 200. The handle 208 includes a body 230 that defines an opening 232 shaped complementary to the shape of the support stand 204, such that the stand 204 can extend through and engage body 230 at the opening 232.

As best shown in exemplary illustrated embodiment of FIGS. 3-6, a steering bar 234 extends outwardly from the body 230 and defines an aperture 235 between the bar 234 and the body 230. The steering bar 234 is formed with transverse portion 236 opposite the body 230 that is joined at each end to the body 230 by a pair of arm portions 238. The transverse portion 236 and arm portions 238 can have any suitable shape, and as illustrated define a aperture 235 therebetween, which in the exemplary configuration is generally trapezoidal in shape, such that the bar 234 also generally conforms to the shape of the container 212 disposed on the support stand 204, minimizing the profile for the assembly 200. In addition, the aperture 235 can include a suitable engagement structure, such as an inwardly sloped inner surface 245, that can engage a complementary structure, such as a curved collar 400, of a container 402 positionable within the aperture 235 adjacent the body 230 to provide additional storage locations for the assembly 200, while maintaining the utility of the steering bar 234. The transverse portion 236 and the arm portions 238 have a continuous cross-section along the entire length of the bar 234, with the exception of a grip 240 located directly opposite the body 230. The grip 240 is formed with a cross-section that generally conforms to the shape of a closed hand of a user to provide and ergonomic shaped section of the bar 234 that can be easily grasped and held by a user to enable the user to steer the assembly 200 using the handle 208. While the grip 240 can have any number of suitable cross-sectional shapes, in the exemplary illustrated embodiment the grip 240 has a narrower cross-section than the bar 234 and includes at least one beveled edge 242 to provide the ergonomic shape to the grip 240.

The bar 234 also includes a number of notches 244 formed thereon. In the illustrated exemplary embodiment of FIGS. 4-6 four (4) notches 244 are disposed adjacent each side of the grip 240 on the transverse portion 236 of the bar 234 and on the arm portion 238 spaced form the transverse portion 236. The notches 244 are disposed on an inner surface 245 of the bar 234 and operate to engage up to four (4) accessory holders 246 that can be attached to the bar 234 at locations in alignment with the notches 244, thus forming perches or holder attachment locations 248. While the accessory holders 246 can be formed from any suitable material, in an exemplary embodiment the holders 246 are formed from a plastic material that has sufficient flex and reduced breakage attributes, along with ease of leaning and/or sterilization, such as a rigid nylon plastic. In other alternative embodiments, alternative engaging structures to be engaged with the holders 246 other than the notches 244 can be disposed at each of the perches or attachment locations 248, or the notches 244 can be omitted entirely at the attachment locations 248 for the securement of the holders 246 to the bar 234 or to any other location of the assembly 200. For example, the holders 246 can be frictionally attached to the bar 234 in a manner that allows the holders 246 to initially be attached to the bar 234 and subsequently slid along the bar 234 to the desired mounting location.

Figure 5:
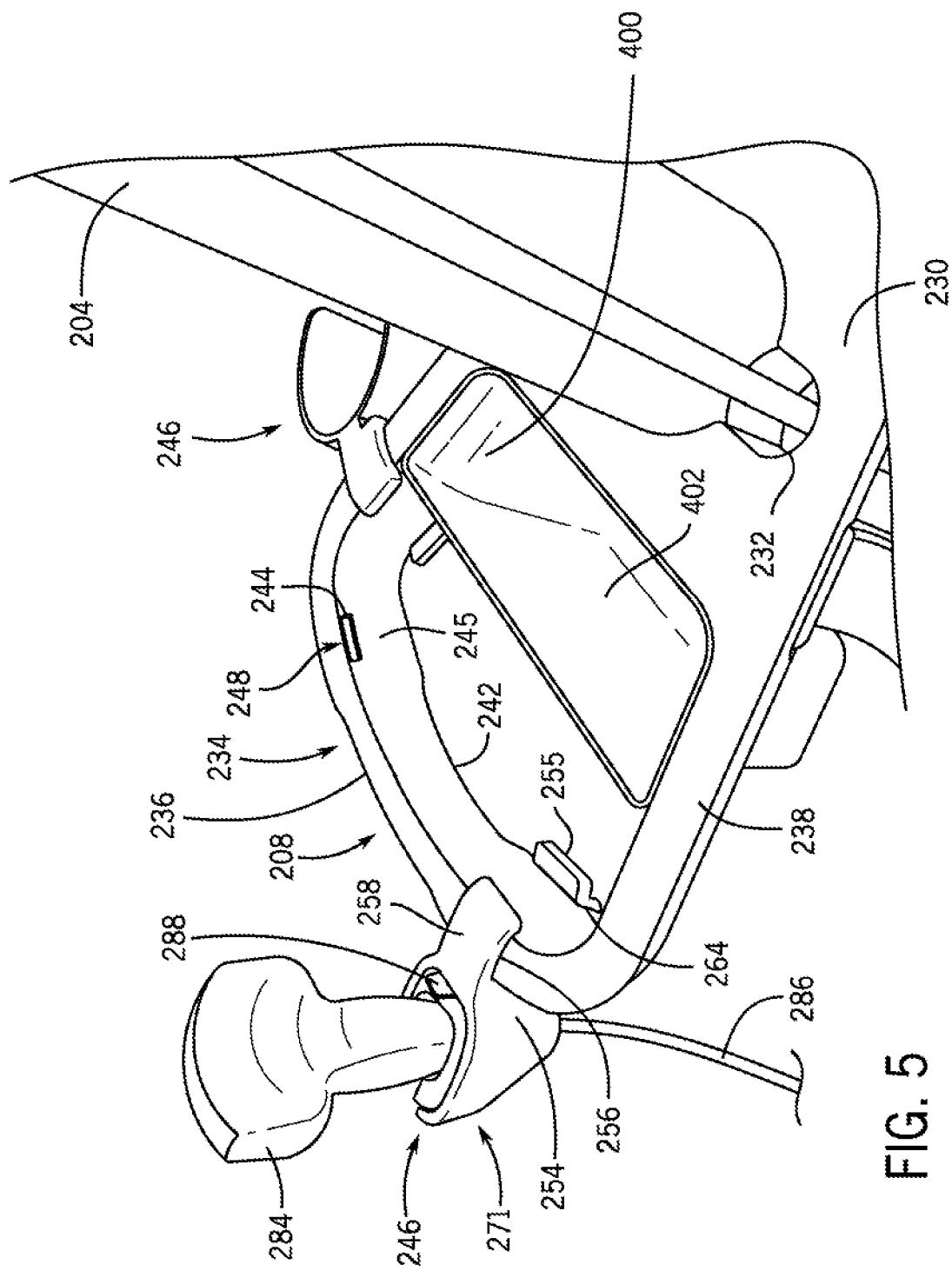
FIG. 5 is a partially broken away isometric view of the central handle and the accessory holders of FIG. 4 in accordance with an embodiment.

The accessory holders 246 are each formed with a body 254 having a clip 256 extending outwardly from one side thereof. The clip 256 includes an upper section 258 and a lower section 264 that define a passage 266 therebetween. The passage 266 is shaped to be complementary to the cross-section of the bar 234, such that the passage 266 can closely conform to the shape of the bar 234. The upper section 258 includes a projection 268 at a distal end of the upper section 258 that can be disposed within a notch 244 on the bar 234 in order to engage the upper section 258 directly with the bar 234. The lower section 264 includes a release tab 269 opposite the body 254 that extends past the bar 234 into the aperture 235 as best shown in FIG. 5. The tab 269 can be engaged and moved/deflected by a user to move the lower section 264 apart from the bar 234 and disengage the clip 256 from the bar 234.

Figure 4:
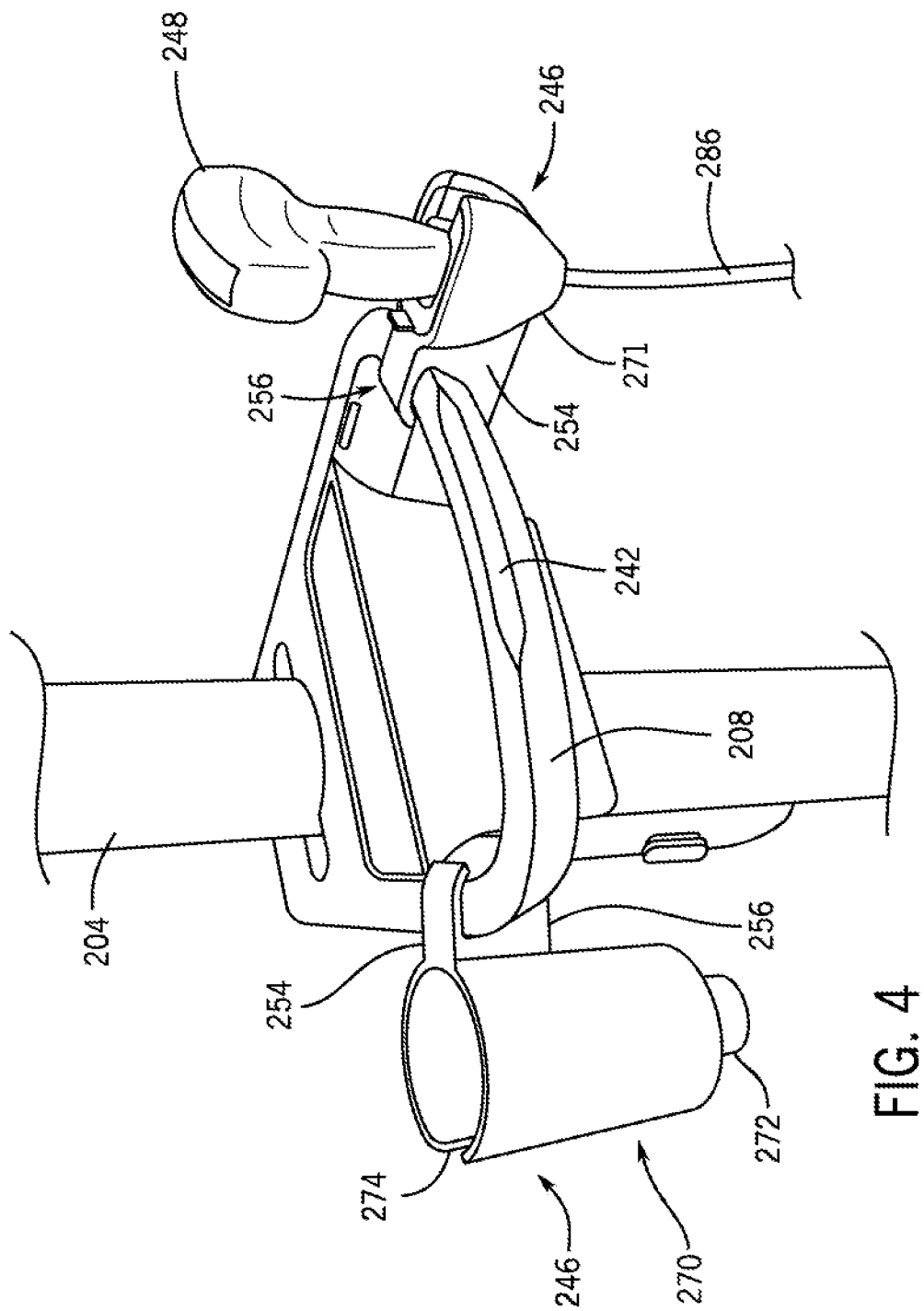
FIG. 4 is a front isometric view of a central handle and accessory holders of the portable ultrasound imaging assembly of FIG. 2 in accordance with an embodiment.
Figure 6:
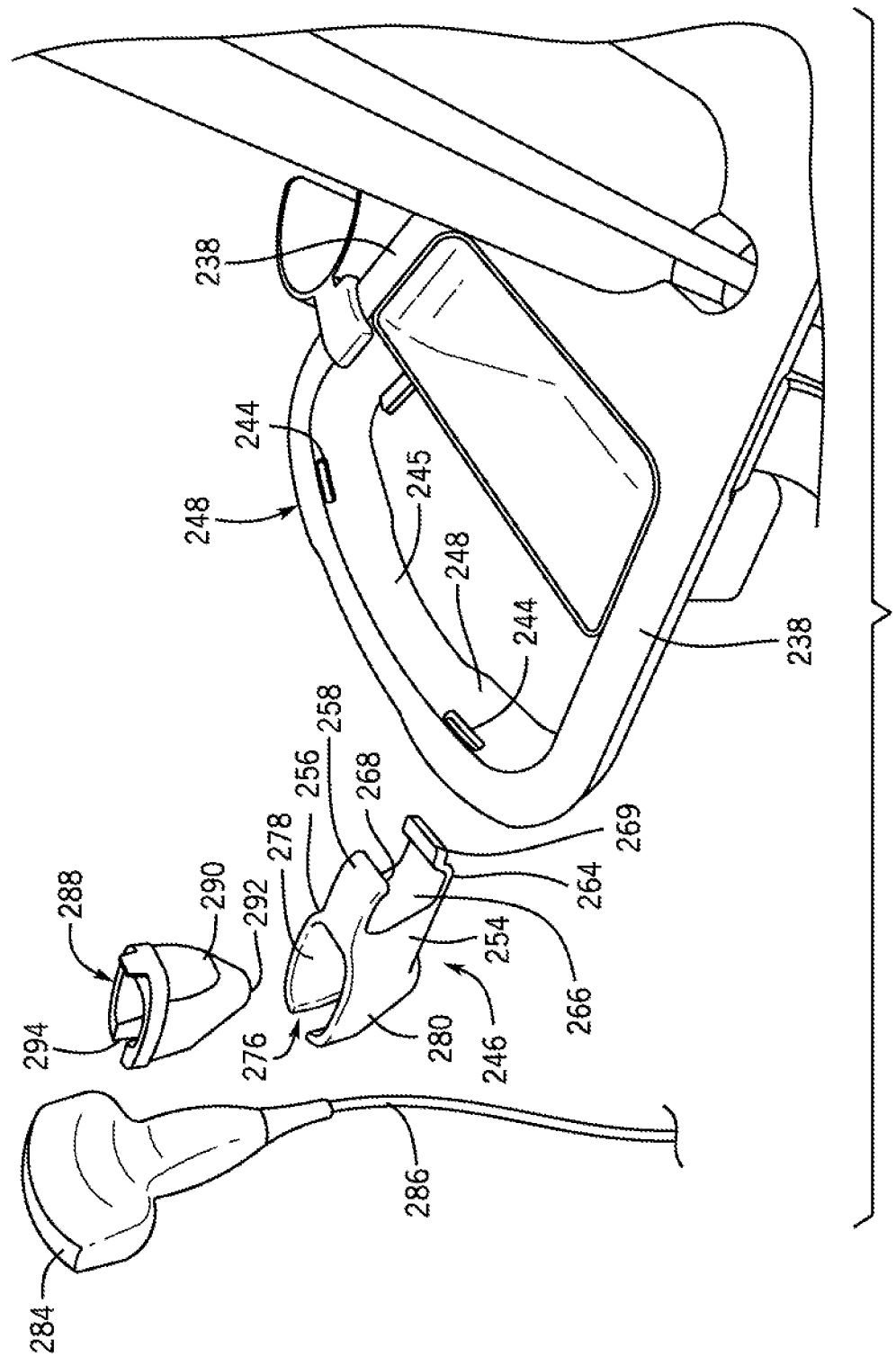
FIG. 6 is a partially broken away isometric view of the central handle and exploded accessory holder of FIG. 4 in accordance with an embodiment.

Opposite the clip 256, each holder 246 includes a cup 270 extending outwardly from the body 254. Alternatively, in this and other embodiments for the holder 246, the body 254 can be omitted entirely and the clip 256 can extend outwardly directly from the cup 270. The cup 270 can have different configurations depending upon the type of accessory or item that is to be releasably positioned within the cup 270. As shown in FIGS. 4-6, in one exemplary embodiment the cup 270 can be shaped to hold a container (not shown) such as bottle of ultrasound gel. The cup 270 has a shape complementary to that for the bottle or container to be disposed therein and includes a drip-catch tray 272 removably positioned at a lower end of the cup 270. The cup 270 additionally includes a slot 274 extending at least partially vertically along the cup 270 opposite the body 254 to facilitate the insertion and removal of the container from within the cup 270.

In another exemplary embodiment for the cup 271 shown in FIGS. 4-6, the cup 270' includes a slot 276 that runs the entire vertical length of the cup 271, separating the cup 271 into opposed halves 278, 280. The cup 271 also includes an opening 282 at the lower end that is intersected by the slot 276. With this configuration, the cup 271 is able to receive and retain a probe 284 therein, with the cord 286 connecting the probe 284 to the ultrasound imaging system 202 able to be inserted and removed from the cup 271 though the slot 276. When the probe 284 is disposed within the cup 271, the cord 286 can extend outwardly from the cup 271 through the slot 276 and opening 282.

In still a further exemplary embodiment for the cup 271, as best illustrated in FIGS. 5 and 6, in order to enable the cup 271 to receive and retain probes 284 having a smaller size, an insert 288 can be disposed within the interior of the cup 271. The insert 288 is formed of any suitable material, such as a rubber and includes a body 290 shaped complementary to the cup 271 with an open lower end 292 and a slot 294 aligned with the slot 276 in the cup 271 to accommodate the cord 286 for the probe 284 placed therein. When positioned within the cup 271, the insert 288 reduces the space within the interior of the cup 271 to allow a smaller probe 284 to be placed within the insert 288 and cup 271, and be held in a stable and elevated position for use in sterile procedures (as no portion of the cup 271 on insert 288 contacts the probe 284 when the probe 284 is positioned therein) and/or to accommodate the use of plastic sheathing on the probe 284, similar to probes 284 disposed within the cups 271 without inserts 288.

Figure 7:
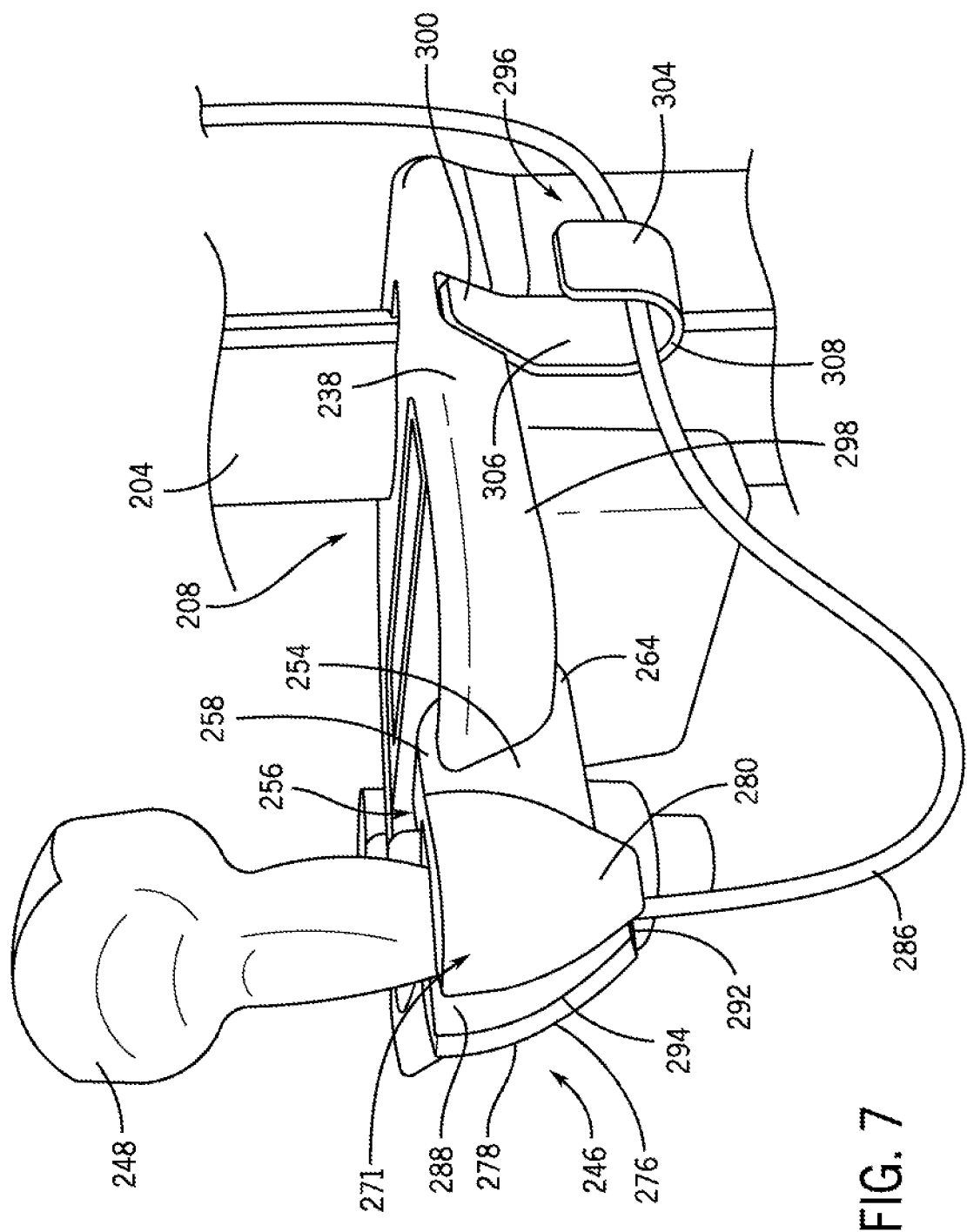
FIG. 7 is a front perspective view of the central handle and a cord hanger of FIG. 4 according to an embodiment.

To assist in managing the cords 286 extending between the cups 271 and the ultrasound imaging system 202, the central handle 208 further includes a number of cord hangers 296 thereon. As shown in the illustrated exemplary embodiment of FIGS. 2, 3 and 7, the hangers 296 are disposed on each arm portion 238 of the handle 208 and are attached to an exterior surface 298 of the arm portions 238 in a suitable manner. The hangers 296 each include a body 300 extending downwardly from the arm portion 238 to a curved section 302 that includes an upwardly extending end 304 disposed opposite the body 300 and that overlaps a portion of the body 300 to define a channel 306 therebetween. The channel 306 is defined to have a depth sufficient to retain a cord 286 therein, as best shown in FIG. 7, and to minimize any inadvertent displacement of the cord 286 out of the channel 306. The channel 304 is open at a top end to enable the cord 286 to be readily removed from within the channel 306 when the probe 284 or other implement associated with the cord 286 is in use. In an alternative embodiment the end 304 can be deflectable or angled towards the body 300 in order to reduce the size of the open end between the body 300 and the end 304, further minimizing the chances for inadvertent displacement of the cord 286 from within the channel 306. In addition, other hangers 297 can be mounted to the assembly 200 in other locations in opposed configurations to hanger 296 in order to form cord wrapping structures that can receive loops of the cords 286 between the hangers 296, 297 to hold the cords in a non-use or storage configuration.

Looking now at FIGS. 1-3, 8 and 9, the ultrasound imaging system 202 is illustrated connected to the cradle 206 disposed on the support stand 204. The system 202 includes an portable imaging device 310 with a display screen 312, such as a touch screen that additionally accommodates user input to the system 202, and a number of plug receptacles 314 disposed opposite the display screen 312. The plug receptacles 314 facilitate connections from various components of the ultrasound imaging assembly 200 to the imaging device 310, such as a plug or connection 316 from a power source 318 disposed below the device 310 on the support stand 204, and plugs or connections 320 at the ends of the cords 286 extending from the various probes 284 and other accessories for use with the ultrasound imaging system 202.

At a top end 322 of the imaging device 310 opposite the cradle 206, the device 310 includes a device carrying handle 324. The device handle 324 is operably connected to and spaced from the device 310, such as by a number of, i.e., one or more, handle supports 326 extending from the device handle 324 and secured to the device 310, and extends transversely along the top end 322 of the device 310, though other configurations and locations for the device handle 324 are also contemplated as being within the scope of the present disclosure. The device handle 324 is formed with a narrow central section 328 and a pair of wider end sections 330. The narrow central section 328 is shaped to accommodate the grasping of the central section 328 by an individual when the device 310 is separated from the cradle 206 (FIGS. 10-13), and to pivot the deuce 310 relative to the support stand 204 when disposed in the cradle 206, The wider end sections 330 are shaped with a cross-section similar to that of the transverse portion 236 and arm portions 238 of the steering bar 234, such that end sections 330 also form perches/holder attachment locations 248. The wider sections 330 can also include notches 244 therein spaced from one another along the wider sections 330 to enable accessory holders 246, including cups 270, 271 and/or inserts 288, to be secured thereto. In the illustrated exemplary embodiment of FIGS. 1-3, 8 and 9, the notches 244 are disposed on the device handle 324 in a position where the holders 246 engaged with the notches 244 are disposed on the handle 324 to extend away from the device 310, thereby maximizing the number of positions at which the holders 246 can be secured to the handle 324 without interfering with the use of the device 310.

Figure 8:
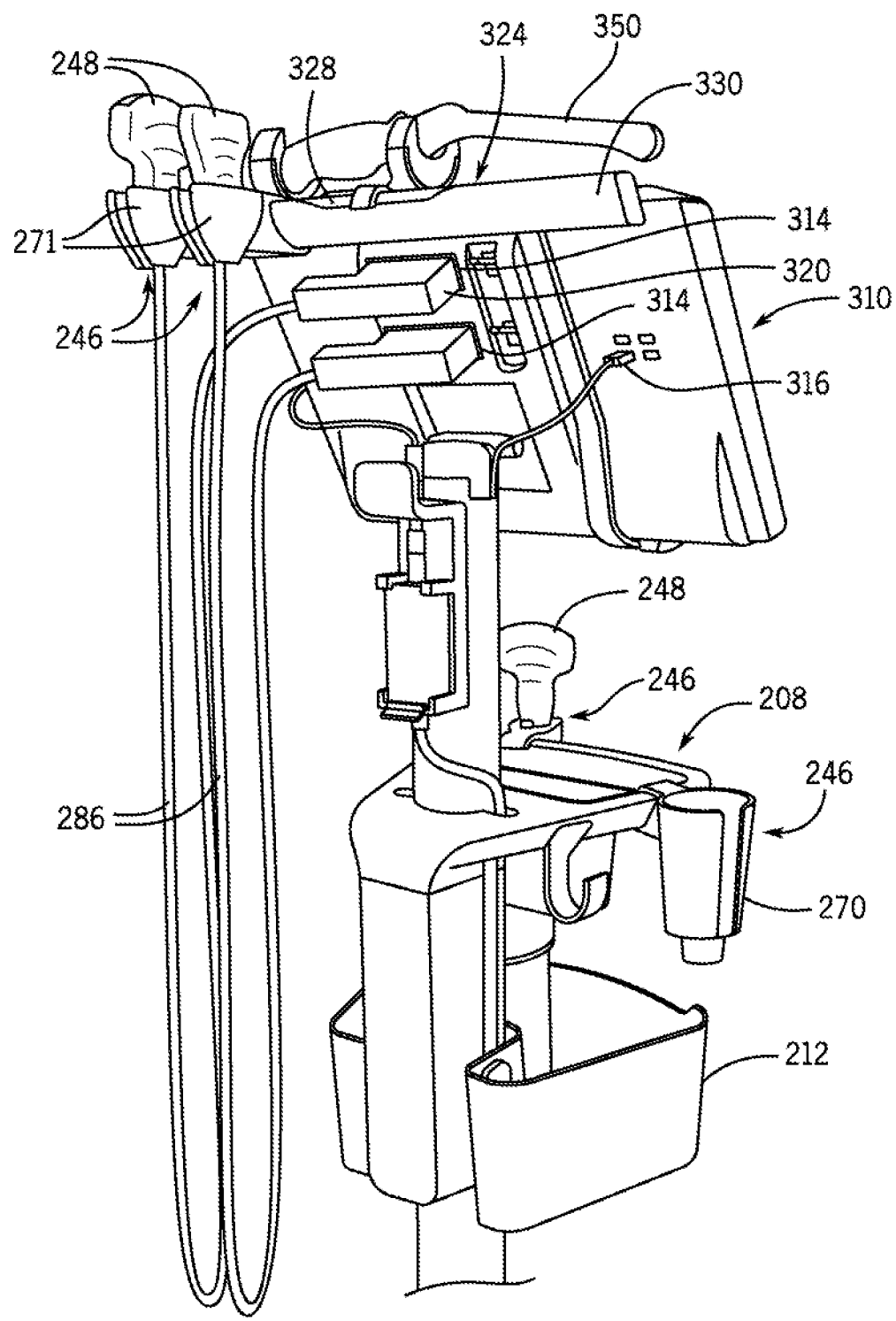
FIG. 8 is a partially broken away, rear isometric view of the portable ultrasound imaging assembly of FIG. 2 in accordance with an embodiment.
Figure 9:
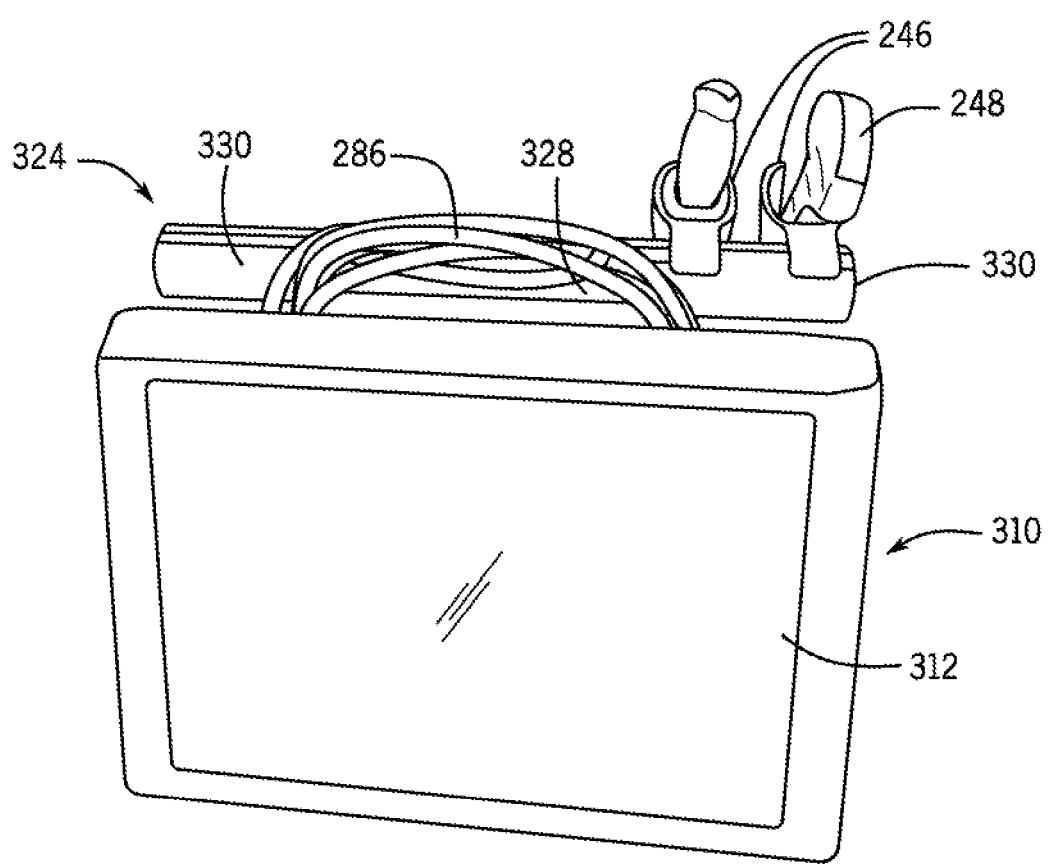
FIG. 9 is a front isometric view of a portable ultrasound device of the portable ultrasound imaging assembly of FIG. 1 in a portable configuration in accordance with an embodiment.
Figure 10:
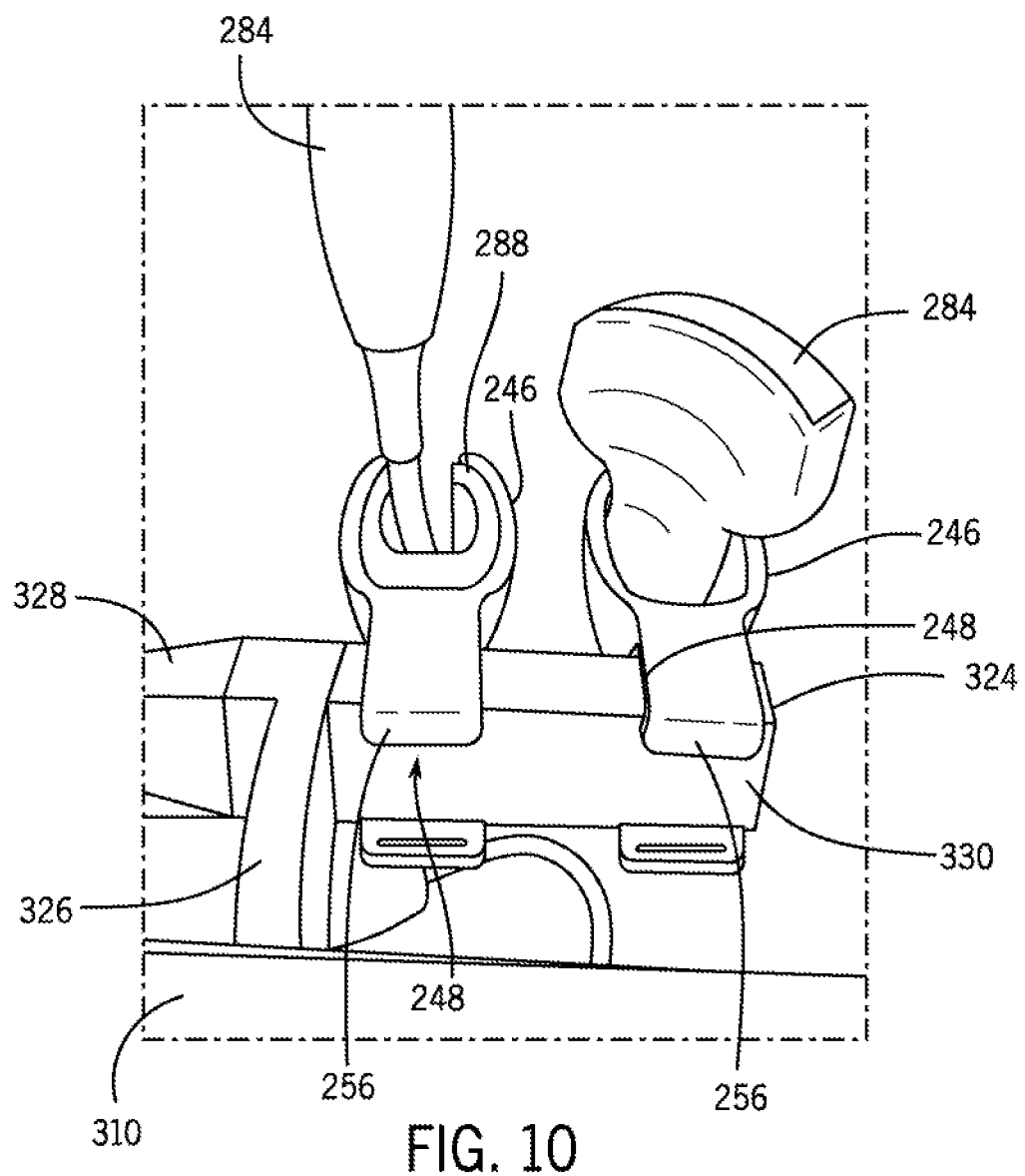
FIG. 10 is a partially broken away, top plan view of a device carrying handle and accessory holders of the portable ultrasound device of FIG. 9 in accordance with an embodiment.
Figure 11:
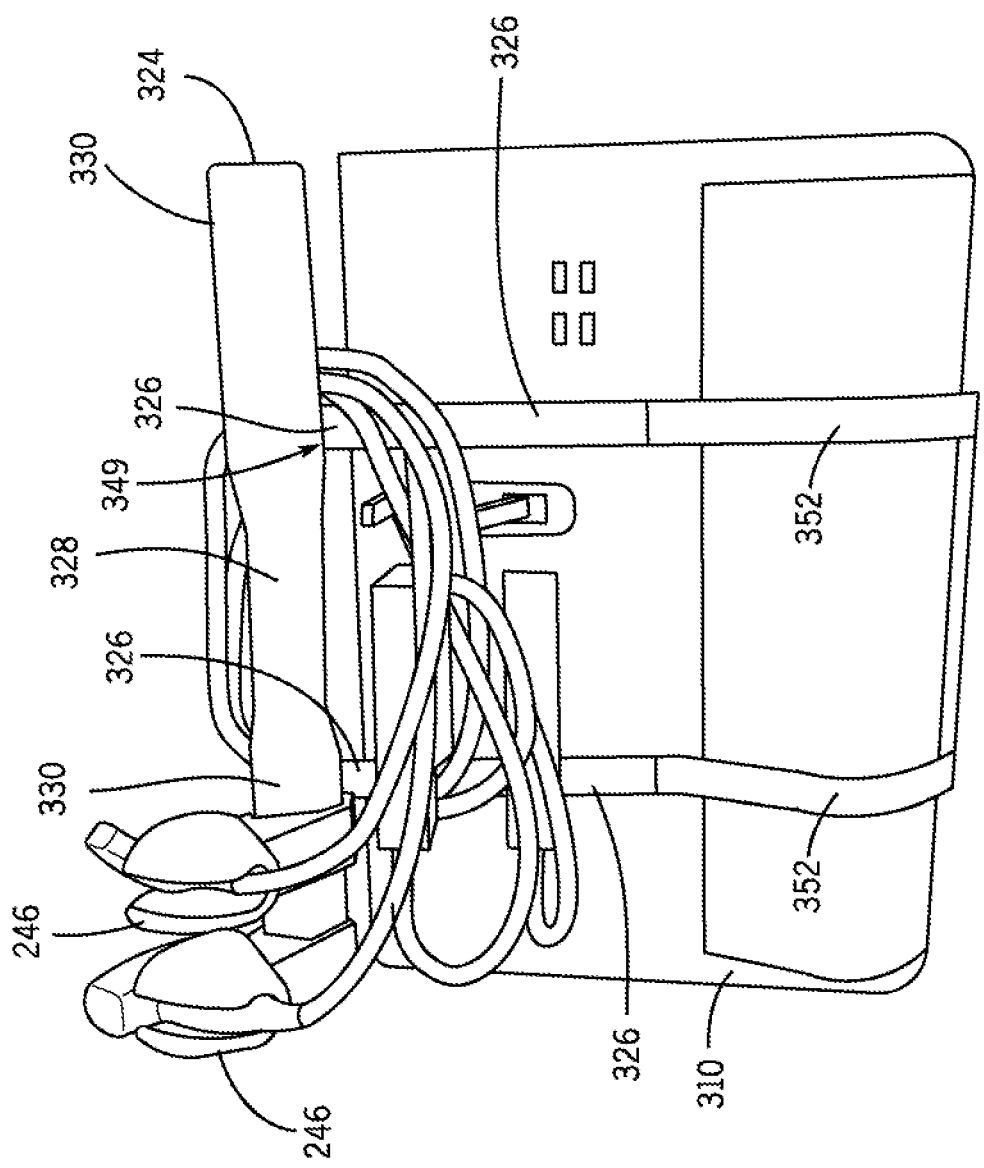
FIG. 11 is a rear isometric view of the portable ultrasound device of FIG. 9 in accordance with an embodiment.
Figure 12:
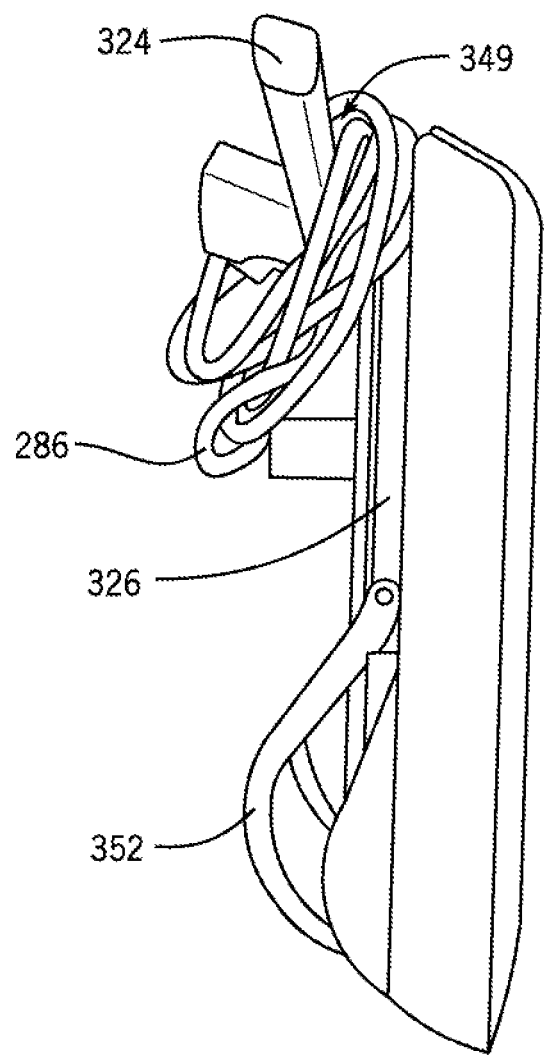
FIG. 12 is a side elevational view of the portable ultrasound device of FIG. 9 including device support legs in a stowed configuration in accordance with an embodiment.
Figure 13:
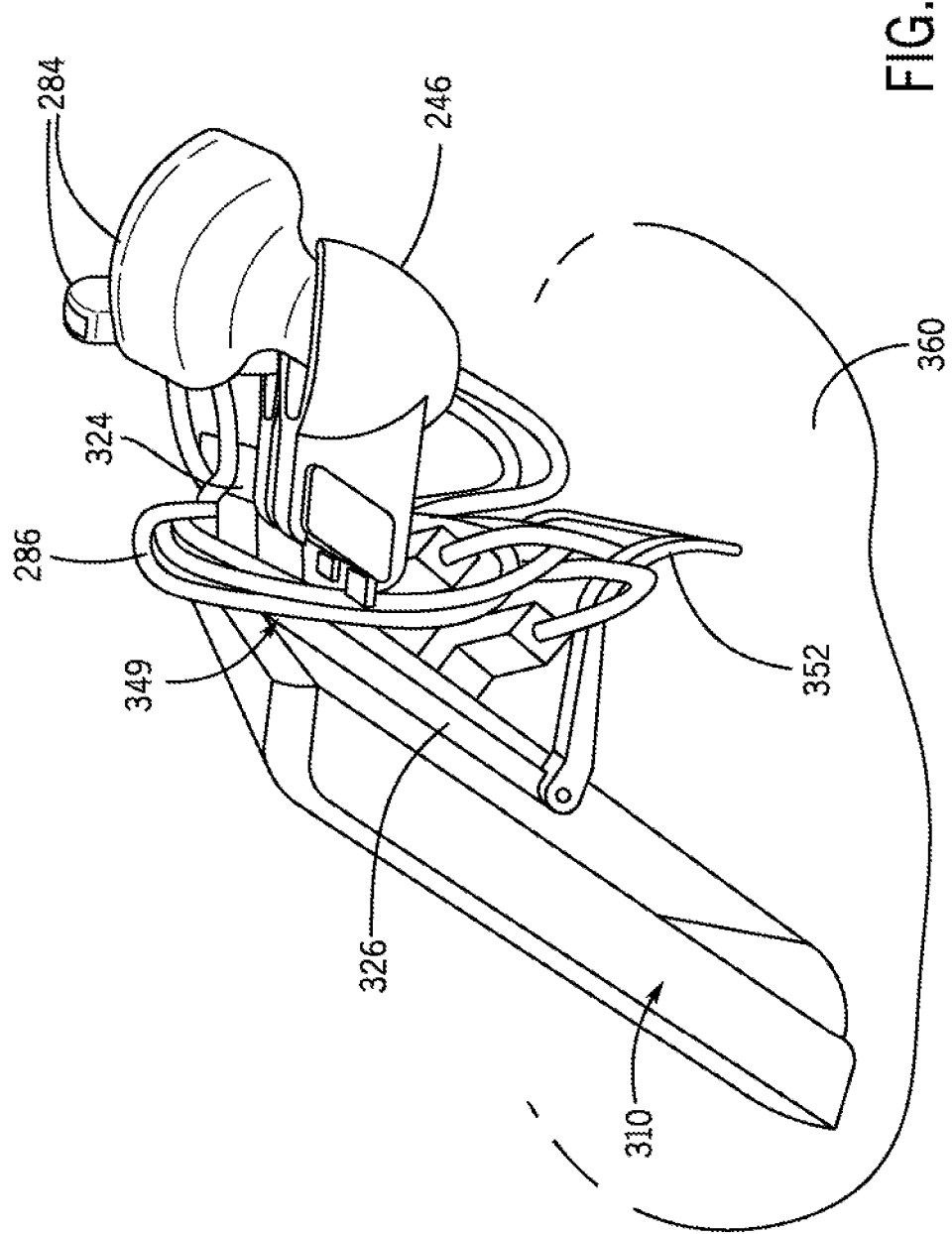
FIG. 13 is a side elevational view of the portable ultrasound device of FIG. 12 with the device support legs in a deployed configuration in accordance with an embodiment.

The device handle 324 also can support an attachment 340, best shown in FIGS. 1 and 8. The attachment 340 is formed similarly to the holders 246 and includes a body 342 extending between a pair of clips 344. The clips 344 are thrilled similarly to the clips 256 on holders 246 and are adapted to securely engage the device handle 324, or notches 244 disposed on the device handle 324. The body 342 includes a pair of resilient supports 346 each extending upwardly from the body 342 and defining a slot 348 therein. The slots 348 are aligned with one another and enable an elongate probe 350, such as an endo-cavity probe, to be securely positioned on the attachment 340. In the illustrated exemplary embodiment, the attachment 340 is disposed on the device handle 324 in an orientation opposed to the holders 246 in order to maximize the space available for the holders 246 and attachment 340 disposed on the device handle 324, while also enabling an individual to readily grasp the central section 328 to manipulate and/or carry the imaging device 310.

As a result of the location of the holders 246 and attachment 340 on the device handle 324, the distance of the device handle 324 from the surface 260 on which the assembly 200 is positioned enables the cords 286 extending between the imaging device 310 and the probes 284, 350 to be held well above the surface 260, event when in held in the associated holder 246 or attachment 340, minimizing and/or eliminating the cords 286 from becoming entangled with one another or from contacting/being run over by the casters 210, and causing damage to the probes 284, 350.

Referring now to FIGS. 10-13, when the imaging device 310 is detached from the cradle 206 and utilized in a portable configuration, the device handle 324 can still support a number of holders 246 and optionally the attachment 340. The holders 246, 340 and associated probes 284, 350 and/or other accessories (e.g., a barcode scanner (not shown)) are retained within the holders 246 while enabling the central section 328 to be grasped by an individual to carry the device 310 and probes 284, 350 held thereon. The cords 286 extending from the probes 284, 350 to the device 310 can be stored by wrapping the cords 286 around the handle supports 326 between the handle 324 and the device 310, which form a cord storage structure 349 and provide a secure and compact storage location for the cords 286.

In addition to providing a storage location of the cords 286 when the device 310 is separated from the cradle 206, the handle supports 326 each include a lower pivoting device support leg or kickstand 352. When the device 310 is to be placed onto a surface 360, such as a table, for use separate from the stand 204, the pivoting device support legs 352 can be moved to a deployed position (FIG. 13) to enable the device 310 to be disposed in more easily viewed, angled position on the surface 360. The pivoting device support legs 352 can subsequently be pivoted back to the stowed position (FIG. 11) when the device 310 is to be moved and/or replaced on the cradle 206 of the assembly 202.

In addition, in an alternative embodiment, mounting locations for the holders on the bar 234 and the device handle 324 can optionally be formed as separate structures from the bar 234 and/or the handle 324 and attached to the stand 204 and/or the imaging device 310 at suitable locations, e.g., below and in front of the device 310 and/or above and behind the device 310, to elevate the cords 286 above the surface 260. The structures (not shown) can function as dedicated perches for attachment of the holders 246, 340 to the assembly 200/imaging system 202/imaging device 310. Also, the holders 246 can be utilized with probes 284 that omit the cords 286, and remotely send information to the ultrasound imaging system 202, or with other corded or cordless accessories having varying shapes and sizes. Further, the sizes and configurations of the holders 246 and/or the cups 270/271 can vary in order to accommodate probes 284, containers, and other accessories of different sizes, with holders 246 and/or cups 270/271 of different sizes being able to be utilized at the same time with the portable ultrasound assembly 200 and/or portable ultrasound system 202 due to the modular nature of the attachment of the holders 246 using the clips 256.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A portable ultrasound imaging system, comprising:
an imaging device;
a number of attachment locations connected to the imaging device; and
at least one accessory holder removably connected to the number of attachment locations,
wherein the at least one accessory holder comprises:
a cup; and
a clip extending outwardly from the cup, wherein the clip is releasably securable to one of the attachment locations,
wherein the clip comprises:
an upper section; and
a lower section spaced from the upper section and defining a passage therebetween, and wherein the passage has a non-circular cross-sectional shape complementary to a cross-sectional shape of at least one portion of a device handle.

2. A portable ultrasound imaging system, comprising:
an imaging device;
a number of attachment locations connected to the imaging device; and
at least one accessory holder removably connected to the number of attachment locations,
wherein the at least one accessory holder comprises:
a cup; and
a clip extending outwardly from the cup, wherein the clip is releasably securable to one of the attachment locations,
wherein the clip comprises:
an upper section; and
a lower section spaced from the upper section and defining a passage therebetween, and
wherein the lower section has a length greater than the upper section and includes a release tab disposed opposite the cup, the release tab extending outwardly from the lower section beyond the length of the upper section.

3. The portable ultrasound imaging system of claim 2, wherein the cup includes a slot extending through the cup opposite the clip.

4. The portable ultrasound imaging system of claim 2, wherein the upper section includes a projection adapted to be received within a notch formed in the attachment location.

5. The portable ultrasound imaging system of claim 2, comprising an insert disposed within the holder.

6. The portable ultrasound imaging system of claim 5, wherein the insert is formed of a rubberized material.

7. The portable ultrasound imaging system of claim 2, comprising a cord hanger connected to the imaging device and adapted to retain a length of a probe cord therein.

8. The portable ultrasound imaging system of claim 2, wherein the number of attachment locations are formed on a device carrying handle secured to the imaging device.

9. The portable ultrasound imaging system of claim 8, comprising at least one handle support connected between the device carrying handle and the imaging device, wherein the at least one handle support forms a cord storage structure between the imaging device and the device carrying handle.

10. The portable ultrasound imaging system of claim 2, comprising:
a support stand to which the imaging device is mounted; and
a central handle secured to the support stand,
wherein the attachment locations are disposed on the central handle.

11. The portable ultrasound imaging system of claim 10, wherein the central handle comprises:
a body secured to the support stand; and
a steering bar extending outwardly from the body and defining an aperture between the steering bar and the body,
wherein the attachment locations are disposed and spaced from one another on the steering bar.

12. A portable ultrasound imaging system, comprising:
a support stand;
a central handle secured to the support stand
an imaging device removably attached to the support stand above the central handle;
a device carrying handle secured to the imaging device; and
at least one accessory holder removably connected to at least one of the central handle and the device carrying handle,
wherein the at least one accessory holder comprises:
a cup; and
a clip extending outwardly from the cup, wherein the clip is releasably securable to one of the central handle or the device carrying
wherein the clip includes a release tab extending outwardly from the clip and defining a flat surface opposite the clip.

13. The portable ultrasound imaging system of claim 12, wherein the clip defines a passage having a cross-sectional shape complementary to a cross-sectional shape of at least one portion of the central handle or the device carrying handle.

14. The portable ultrasound imaging system of claim 12, comprising an insert disposed within the accessory holder.

15. The portable ultrasound imaging system of claim 12, comprising a cord hanger connected to the central handle.

16. The portable ultrasound imaging system of claim 12, comprising at least one handle support connected between the device carrying handle and the imaging device, wherein the at least one handle support forms a cord storage structure between the imaging device and the device carrying handle.

* * * * *